Figure 1:
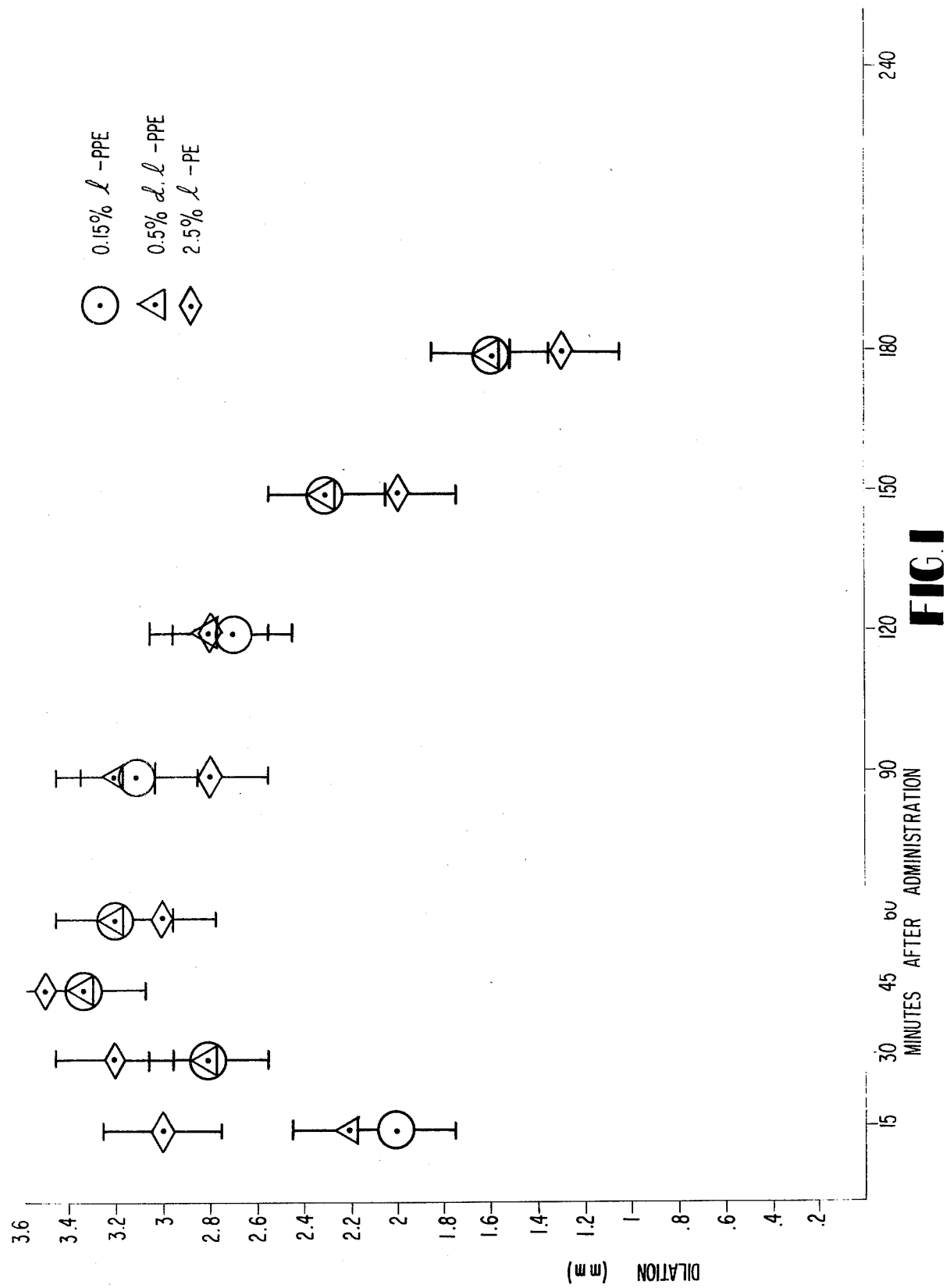

United States Patent [19]

Bodor et al.

[11] 4,088,783
[45] May 9, 1978

[54] NOVEL OPTICALLY ACTIVE M-ACYLOCY-α-[(METHYLAMINO)METHYL]BENZYL ALCOHOLS AND THE PHARMACEUTICALLY ACCEPTABLE ACID ADDITION SALTS THEREOF

[75] Inventors: Nicolae S. Bodor; Sun-Shine Yuan, both of Lawrence, Kans.

[73] Assignee: INTERx Research Corporation, Lawrence, Kans.

[21] Appl. No.: 732,978

[22] Filed: Oct. 18, 1976

Related U.S. Application Data

[60] Division of Ser. No. 578,079, May 16, 1975, abandoned, which is a continuation-in-part of Ser. No. 548,606, Feb. 10, 1975, Pat. No. 3,966,749.

[51] Int. Cl.² ............... A61K 31/225; C07C 91/34
[52] U.S. Cl. ............... 424/313; 260/293.66; 260/307 F; 260/404; 560/60; 560/109; 560/142
[58] Field of Search ............... 260/479 S; 424/313

[56] References Cited
U.S. PATENT DOCUMENTS 3,825,583   7/1974   Hussain et al. ............... 260/479 R

*Primary Examiner*—Jane S. Myers
*Attorney, Agent, or Firm*—Bacon & Thomas

[57] ABSTRACT

Compounds of the formula:

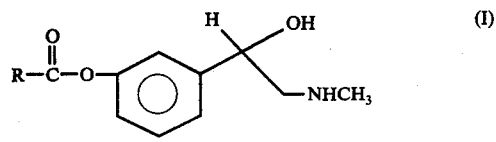

wherein R represents a member selected from the group consisting of a straight or branched alkyl group of from one to 20 carbon atoms ($C_1$-$C_5$ being preferred), an ethoxycarbonyl group, a benzyloxycarbonyl group, a phenyl group, an

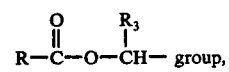

wherein R is as defined above and $R_3$ is a member selected from the group consisting of a hydrogen atom, a methyl group and a phenyl group, and a 2-, 3-, or 4-pyridyl group, or the HX salts thereof, wherein X represents a pharmaceutically acceptable acid addition salt anion, are extremely valuable in the treatment of conditions responsive to sympathomimetic agents.

The compounds of this invention find therapeutic application to warm-blooded animals (e.g., humans) in the management of asthma, nasal congestion and as decongestants, vasoconstrictors, mydriatic agents, and anti-glaucomatous agents in the practice of opthalmology.

Upon administration, these compounds will enzymatically "cleave," thus releasing optically active phenylephrine (m-hydroxy-α-[(methylamino)methyl]benzyl alcohol, the therapeutically active moiety thereof.

15 Claims, 1 Drawing Figure

NOVEL OPTICALLY ACTIVE M-ACYLOCY-α-[(METHYLAMINO)METHYL]-BENZYL ALCOHOLS AND THE PHARMACEUTICALLY ACCEPTABLE ACID ADDITION SALTS THEREOF

CROSS REFERENCE TO RELATED APPLICATIONS

This application is a divisional application of Ser. No. 578,079, filed May 16, 1975, now abandoned, which in turn is a continuation-in-part application of Ser. No. 548,606, filed Feb. 10, 1975, now U.S. Pat. No. 3,966,749.

BACKGROUND OF THE INVENTION

1. Field of the Invention

The present invention is directed to certain esters of m-hydroxy-α-[(methylamino)methyl]benzyl alcohols and their pharmaceutically acceptable acid addition salts.

Upon administration, these compounds will enzymatically "cleave" and release optically active m-hydroxy-α-[(methylamino)-methyl]benzyl alcohol (phenylephrine), the therapeutically active moiety thereof.

2. Description of the Prior Art

U.S. Pat. No. 3,825,583 — Hussain and Truelove, discloses and claims an ester of m-hydroxy-α-[(methylamino)methyl]benzyl alcohol, namely, m(3-)-pivaloxy-α-[(methylamino)methyl]benzyl alcohol.

A review of the manner in which this compound is prepared readily reveals that a racemic mixture (a mixture containing both the biologically active and the biologically non-active isomer) is obtained. Since the "R" isomer is the only isomer exhibiting substantial therapeutic activity, to date, (R)-m-pivaloxy-α-[(methylamino)methyl]benzyl alcohol is normally administered in the form of a racemic mixture as the means to separate the optically active form from the racemic mixture has not been devised to date.

Therefore, a need exists for a means to synthesize the optically active form of certain m-acyloxy-α-[(methylamino)methyl]benzyl alcohols of which m-pivaloxy-α-[(methylamino)methyl]benzyl alcohol is so among and thus avoid the need to obtain and use a racemic mixture thereof.

In addition to the foregoing, it is obviously apparent that since only the active isomer of the compounds described herein is therapeutically active, the dosage amount of a racemic mixture containing the same required to achieve therapeusis is much greater than that which would be required if the optically active form were administered, per se. Thus, an ancillary need exists for a means to synthesize the optically active isomer, per se, for the sake of minimizing the therapeutic dose required as well as to avoid any toxic reactions which may occur.

SUMMARY OF THE INVENTION

It is, therefore, the primary object of the present invention to synthesize and obtain the optically active form of certain m-acyloxy-α-[(methylamino)methyl]-benzyl alcohols as described herein, which upon administration to a warm-blooded animal (e.g., human) will enzymatically "cleave" to release optically active phenylephrine, the therapeutically active moiety thereof.

It is another object of the present invention to synthesize and obtain the above-described optically active forms so as to enable therapeusis to be achieved with a lesser dose of the optically active form over a racemic mixture containing the same.

These and other obvious objects are achieved via the synthesis scheme set out below.

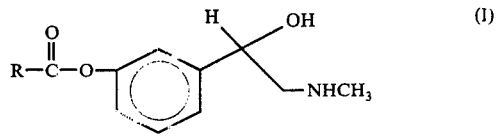

(I)

wherein R represents a member selected from the group consisting of a straight or branched alkyl group of from one to 20 carbon atoms ($C_1$–$C_5$ being preferred), an ethoxycarbonyl group, a benzyloxycarbonyl group, a phenyl group, an

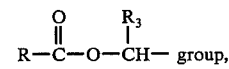

group, wherein R is defined as above and $R_3$ represents a member selected from the group consisting of a hydrogen atom, a methyl group and a phenyl group, and a 2-, 3-, or 4-pyridyl group, or the HX salts thereof, and wherein X represents a pharmaceutically acceptable acid addition salt anion derived from the corresponding acid (e.g., chloride, bromide, sulfate, sulfonate, phosphate, nitrate, acetate, propionate, succinate, glycolate, stearate, lactate, tartrate, citrate, ascorbate, pamoate, maleate, hydroxymaleate, phenylacetate, glutamate, benzoate, salicylate, sulfonilate, fumarate, toluenesulfonate, etc.) are prepared by:

(1) reacting optically active phenylephrine with an excess of a carbonyl compound of the formula: $R_1$—CO—$R_2$, wherein $R_1$ and $R_2$ which can be the same or different and represent a member selected from the group consisting of a hydrogen atom, a $C_1$–$C_{10}$ alkyl group, and a di($C_1$–$C_2$)alkylamino($C_1$–$C_{10}$)alkyl group, or wherein $R_1$ and $R_2$ together with the carbonyl group to which they are attached can form a member selected from the group consisting of a $C_5$–$C_7$ cycloalkanone group (pentanone, hexanone, or heptanone) and a substituted or unsubstituted N- or O-heterocyclic($C_5$–$C_7$) alkanone group (e.g., piperidone, pyrrolidone, N-methylpiperidone, or N-methylpyrrolidone, etc.), wherein said substituent is a $C_1$–$C_2$ alkyl group, either in the presence of a dehydrating agent selected from the group consisting of, but not limited to an alkaline earth metal carbide (calcium carbide, magnesium carbide, etc), a molecular sieve of from 4 to 5 A, calcium chloride, magnesium sulfate, and sodium sulfate, or in the presence of a conventional inert aromatic hydrocarbon solvent (e.g., benzene, toluene, xylene, etc.) plus an organic or inorganic acid catalyst (e.g., p-toluenesulfonic acid, sulfosalicylic acid, benzenesulfonic acid, sulfuric acid, hydrochloric acid, etc.) to eliminate the water formed as an azeotropic mixture, said steps being carried out at a temperature of from 20° to 140° C (preferably, however, at the boiling point of the solvent or solvent mixture employed), standard pressure, and for a period of time ranging from 2 to 48 hours, whereby the intermediate:

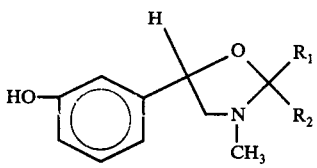

wherein $R_1$ and $R_2$ are defined as above is formed;

(2) reacting the intermediate of step (1) with a member selected from the group consisting of an M-hydroxide, an M-hydride, and an M-alkoxide, wherein M represents a member selected from the group consisting of an alkali metal, an alkaline earth metal, and thallium (e.g., NaOH, KOH, Ca(OH)$_2$, Mg(OH)$_2$, Ba(OH)$_2$, NaH, CaH$_2$, NaOCH$_3$, NaOC$_2$H$_5$, NaOC$_3$H$_7$, TlOC$_2$H$_5$, etc.) in the presence of an inert organic solvent selected from the group consisting of an aliphatic hydrocarbon solvent of from five to 10 carbon atoms (e.g., pentane, hexane, heptane, octane, decane, etc.), an aromatic hydrocarbon solvent (e.g., benzene, toluene, xylene, etc.), and C$_1$-C$_4$ aliphatic alcohol (methanol, ethanol, propanol, butanol), a conventional ether (e.g., diethyl ether, tetrahydrofuran, dioxane, etc.) and dimethylformamide, etc., said step being carried out at room temperature, standard pressure, and for a period of time ranging from 1 to 24 hours, whereby the intermediate:

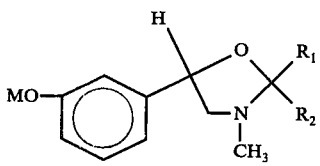

wherein M, $R_1$, and $R_2$ are defined above is formed;

(3) reacting the intermediate of step (2) with a stoichiometric amount of an acyl halide of the formula: R—CO—Y, wherein R is defined as above and Y represents a halogen atom (chlorine, bromine, iodine) in the presence of an inert organic solvent selected from the group consisting of an aliphatic hydrocarbon solvent of from five to ten carbon atoms, an aromatic hydrocarbon solvent (e.g., benzene, toluene, xylene, etc.), methanol, propanol, butanol, a conventional ether (e.g., diethyl ether, tetrahydrofuran, dioxane, etc.), or dimethylformamide, said step being carried out at room temperature, standard pressure, and for a period of time ranging from 1 to 24 hours, whereby the intermediate:

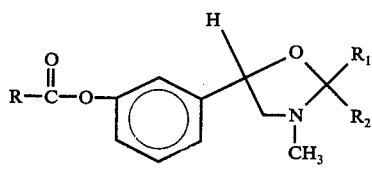

wherein R, $R_1$, and $R_2$ are defined as above is formed; and (4) cleaving the $R_1$—CO—$R_2$ moiety of the intermediate from step (3) in an organic inert solvent selected from the group consisting of an aliphatic hydrocarbon solvent of from five to 10 carbon atoms, an aromatic hydrocarbon solvent (e.g., benzene, toluene, xylene, etc.), a C$_1$-C$_4$ aliphatic alcohol, a conventional ether (diethyl ether, tetrahydrofuran, dioxane, etc.), and dimethylformamide and further in the presence of a stoichiometric or excess amount of water and a catalytic amount (normally but not absolutely, 0.01–1.0% of the stoichiometric amount) of an HX acid, wherein X is defined as above, said step being carried out at a temperature of from 20° to 100° C, standard pressure, and for a period of time of from 1 to 24 hours, whereby the free base of formula (I) is obtained; and (5) optionally, replacing the catalytic amount of the HX acid in step (4) with the stoichiometric amount of the same, whereby the HX salt of the free base of the compound represented by formula (I) is obtained.

The synthesis procedure outlined above is discussed in detail in our copending application, Ser. No. 548,606, filed Feb. 10, 1975.

The compounds of this invention find therapeutic application to warm-blooded animals (e.g., humans) in the management of asthma nasal congestion, and as decongestants, vasoconstrictors, mydriatic agents, and anti-glaucomatous agents in the practice of ophthalmology. Upon administration, they will enzymatically "cleave" and release phenylephrine, the therapeutically active moiety thereof.

The phrase, "pharmaceutically acceptable acid addition salt" as used herein generally includes the non-toxic acid addition salts of the compounds of formula (I), formed with non-toxic inorganic salts or organic acids. For example, the salts include those derived from inorganic acids such as hydrochloric, hydrobromic, sulfuric, sulfamic, phosphoric, nitric and the like; and the salts prepared from organic acids such as acetic, propionic, succinic, glycollic, stearic, lactice, malic, tartaric, citric, ascorbic, pamoic, maleic, hydroxymaleic, phenylacetic, glutamic, benzoic, salicylic, sulfanilic, fumaric, toluene-sulfonic, and the like.

EXAMPLE I

PREPARATION OF OPTICALLY ACTIVE m-(TRIMETHYLACETOXY)-α-[(METHYLAMINO)METHYL]BENZYL ALCOHOL HYDROCHLORIDE (R)-phenylephrine (9.0 g, 0.05 mole), acetone (1 liter) and calcium carbide (4.0 g, 0.06 mole) were heated together at reflux with stirring for 24 hours. The solid material formed was filtered off and the filtrate was concentrated in vacuo. The residue was crystallized in an acetone-hexane mixture to give 7.0 g of (R)-2,2,3-trimethyl-5-(m-hydroxyphenyl)-1,3-oxazolidine, 70% yield. mp 118°–120° C, $\alpha_D^{25°} = -17.9°$ (CH$_3$OH), ir (KBr): 2980, 2860, 2700, 1600, 1450, 1260 and 1120 cm$^{-1}$. nmr (CD$_3$COCD$_3$): δ 7.4 – 6.6 (m, 4H), 5.2 (b, 1H), 5.0 (t, 1H, J = 7Hz), 3.3 (dd, 1H, J = 7 and 9Hz), 2.7 (dd, 1H, J = 7 and 9Hz), 2.4 (s, 3H) and 1.3 (s, 6H) ppm.

Anal. Calcd for C$_{12}$H$_{17}$NO$_2$: C, 69.6; H, 8.2; N, 6.8. Found: C, 70.3; H, 8.4; N, 6.7.

To a solution of the (R)-2,2,3-trimethyl-5-(m-hydroxyphenyl)-1,3-oxazolidine previously obtained (1.32 g, 6.38 mmole) in 60 ml of ether, there was added thallous ethoxide (1.59 g, 6.38 mmole) and the mixture was stirred at room temperature for 1 hour. Pivalyl chloride (0.79 ml, 6.38 mmole) was then added and stirring was maintained for 2 additional hours. The solid material formed in the reaction was filtered and the filtrate (this solution was usually used directly in the next reaction without evaporation) was evaporated to dryness to give 1.8 g of an oily product, (R)-2,2,3-trimethyl-5-(m-trimethylacetoxyphenyl)-1,3-oxazolidine, 95% yield. $\alpha_D^{25°} =$ −10.6° (C₂H₅OH). ir(neat): 2960, 1760, 1610, 1590, 1480, 1450, 1370, 1360, 1260, 1230, 1140, and 1105 cm$^{-1}$. nmr (CCl₄): δ 7.4 – 6.8 (m, 4H), 5.0 (t, 1H, J = 7Hz), 3.3 (dd, 1H, J = 7 and 9Hz), 2.8 (dd, 1H, J = 7 and 9Hz), 2.3 (s, 3H), 1.4 (s, 9H) and 1.3 (s, 6H) ppm.

The filtrate obtained in the previous reaction containing (R)-2,2,3-trimethyl-5-(m-trimethylacetoxyphenyl)-1,3-oxazolidine (1.8 g, 6.2 mmole) in 60 ml of ether was treated with hydrogen chloride gas until the solution was no longer turbid. This mixture was then evaporated to dryness and the residue was dissolved in a small amount of ethanol and then diluted with hexane. The hydrolysis and crystallization took place in the solution to give 1.2 g of the final product, (R)-m-(trimethylacetoxy)-α-[(methylamino)methyl]benzyl alcohol hydrochloride, 70% yield. mp 128°–130° C, $\alpha_D^{25°}$ = −36.7° (C₂H₅OH). ir (KBr): 3370, 2960, 2795, 2420, 1750, 1610, 1590, 1460, 1240 and 110 cm$^{-1}$. nmr (CD₃COCD₃. D₂O): δ 7.5 – 6.8 (m, 4H), 5.3 (dd, 1H, J = 5 and 10Hz), 3.8 (b, 3H), 3.4 (m, 2H), 2.9 (s, 3H) and 1.4 (s, 9H) ppm.

Anal. Calcd for C₁₄H₂₂NO₃Cl: C, 58.4; H, 7.7; N, 4.9. Found: C, 58.4; H, 7.7; N, 4.6.

The remaining compounds of formula (I) can be prepared with similar success by substituting the generically or specifically described reactants and/or operating conditions of this invention for those used in the preceding example. Similarly, this process can be used to prepare the enantiomeric(S)-isomers or the racemic (R,S)-isomers as well.

EXAMPLE II

HYDROLYSIS (CLEAVAGE) OF OPTICALLY ACTIVE m-(TRIMETHYLACETOXY)-α-[(METHYLAMINO)METHYL]BENZYL ALCOHOL HYDROCHLORIDE TO OPTICALLY ACTIVE PHENYLEPHRINE (m-HYDROXY-α-[(METHYLAMINO)METHYL]BENZYL ALCOHOL)

The following study clearly evidences the fact that the compounds of the instant invention hydrolytically "cleave," thus releasing (R)-phenylephrine hydrochloride, the therapeutic moiety of the initial compound.

(R)-m-(trimethylacetoxy)-α-[(methylamino)methyl]benzyl alcohol hydrochloride obtained from Example I (1.0 g) was dissolved in 10 ml of methanol containing 1 ml of concentrated hydrochloric acid. The resulting solution was then refluxed for 24 hours, and subsequently, the solvent was then removed in vacuo to give 0.7 g (90% yield) of (R)-phenylephrine as determined by conventional optical activity determination procedures.

$\alpha_D^{25°}$ = −47.0° (Lit. $\alpha_D^{25°}$ = −46.2, Dictionary of Organic Compounds 4th Ed. Oxford University Press, 1965).

EXAMPLE III

MYDRIATIC STUDIES

Standard doses of 50 μl of the following isotonic solutions were applied onto male and female rabbit eyes: 0.15% of (R)-m-(trimethylacetoxy)-α-[(methylamino)methyl]benzyl alcohol hydrochloride (l-PPE, this invention); 0.5% of a racemic mixture of m-pivaloxy-α-[(methylamino)methyl]benzyl alcohol hydrochloride (d,l-PPE) — U.S. Pat. No. 3,825,583; and 2.5% of (R)-phenylephrine hydrochloride (l-PE). All of the compounds tested elicited the same mydriatic response as can be seen from a review of FIG. 1 accompanying the instant application. Thus, it is clearly established that the compounds of this invention easily elicit a mydriatic response at a much lesser dosage rate than that observed for its closest competitors (m-pivaloxy-α-[(methylamino) methyl]benzyl alcohol hydrochloride) or phenylephrine hydrochloride, per se.

By following the above procedure, equivalent mydriatic responses will be observed for the remaining compounds of formula (I).

The compounds prepared by the process of the instant invention can be used by the pharmaceutical and/or veterinary arts for the treatment of glaucoma, bronchial asthma, and nasal decongestion associated with hay fever and allergic rhinitis in warm-blooded animals (e.g., humans) in a variety of pharmaceutical preparations as described in U.S. Pat. No. 3,825,583.

The novel compound and its pharmaceutically acceptable salts can be used by the pharmaceutical and the veterinary arts for ophthalmological treatment and for treating bronchial asthma including hay fever and allergic rhinitis in a variety of pharmaceutical preparations. The new compound and its non-toxic salts are thus administrable in the form of injectables, tablets, capsules, solutions, suppositories, ointments, emulsions, jellies, buccal patches, oral inhalants, nasal inhalants, aerosols, and in other suitable forms. The pharmaceutical or veterinary preparation which contains the compound is conveniently admixed with from about 0.1 micrograms to 10 grams of a non-toxic pharmaceutical organic or inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as disintegrates, binders, emulsifiers, preservatives, wetting agents, bodying agents and the like, as for example, polyethylene glycols 200, 300, 400 and 600, carbowaxes 1,000, 1,500, 4,000 and 10,000, bacterial components such as quaternary ammonium compounds, phenylmercuric salts known to have cold sterilizing properties and which are non-injurious in use, thimerosal, propyl paraben, buffering ingredients such as sodium chloride, sodium borate, sodium acetate, gluconate buffers, and other conventional ingredients such as sorbitan monolaurate, triethanolamine oleate, polyoxyethylene sorbitan monopalmitylate, dioctyl sodium sulfosuccinate, monothioglycerol, thiosorbitol, ethylenediamine tetracetic acid, and the like. Additionally, suitable vehicles can be used as carrier media for the present purpose including conventional phosphate buffer vehicle systems, isotonic boric acid vehicles, isotonic sodium chloride vehicles, isotonic sodium borate vehicles, and the like.

As for the therapeutic dose required of the compounds prepared by the process of the instant invention, while dosage limitations will naturally vary with the size and needs of the individual treated, normally, the dosage range will mimic that described for the racemic compound m-pivaloxy-α-[(methylamino)methyl]benzyl alcohol as described in U.S. Pat. No. 3,825,583. However, therapeusis has been observed with as much as ⅓ the dose of m-pivaloxy-α-[(methylamino)methyl]benzyl alcohol (racemic) as well. Thus, to be specific, the dose administered, whether a single dose or a daily dose, will, of course, vary because of the chosen route of administration, and the size of the recipient. The dosage administered is not subject to definite bounds, but it will usually be an effective amount, or the equivalent on a molar basis of the pharmacologically active form produced upon the metabolic release of the active drug to achieve its desired pharmacological and physiological effect. Generally a range of from 0.01% to 10.0% will suffice. However, the following illustrations will further serve to set the parameters. The medical dose for warm-blooded mammals, including humans and primates by the intramuscular or subcutaneous route will be about 100 micrograms to 5 milligrams administered in 0.1 to 1.5 ml of a 0.1 to 0.5% oil suspension, with the usual intramuscular dose of 200 to 750 micrograms in 0.2 to 0.75 ml of a 0.1 to 0.5% solution. For oral inhalation the dose is about 0.01 to 2.0% applied as a fine mist. For typical application in operative procedures on the nose and throat, solutions of 0.002 to 0.97% may be used. For typical oral administration, 5 mgm to 250 mgm may be used in tablets or capsules. Generally, the dosage form for a typical non-toxic salt, for example, the hydrochloride in a solution intended for inhalation will be about 0.025 to 4% and the like. The dose for farm animals is generally about 4 to 10 ml by the subcutaneous or intramuscular route for horses and cattle and for dogs about 0.2 to 0.6 ml, and the like.

It should be specifically emphasized that the optically active compounds of the instant invention are optically pure to the extent that only the levorotatory compound (R)-(-) is obtained. This is due to the ability of the present inventors to utilize levorotatory (R)-(-)-phenylephrine initially and maintain levorotation throughout the synthesis. Heretofore this has not been possible.

From the foregoing description, one of ordinary skill in the art can easily ascertain the essential characteristics of this invention, and without departing from the spirit and scope thereof, can make various changes and/or modifications of the invention to adapt it to various usages and conditions. As such, these changes and/or modifications are properly, equitably, and intended to be, within the full range of equivalence of the following claims.

What we claim is:

1. An optically pure and biologically active levorotatory compound of the formula:

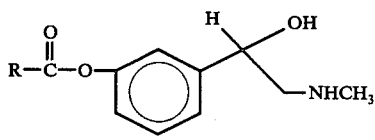

wherein R represents a member selected from the group consisting of an ethoxycarbonyl group and a benzyloxycarbonyl or the HX salts thereof, wherein X represents a pharmaceutically acid acceptable addition salt anion.

2. A pharmaceutical composition comprising a sympathomimetically effective amount of an optically pure and biologically active levorotatory compound of the formula:

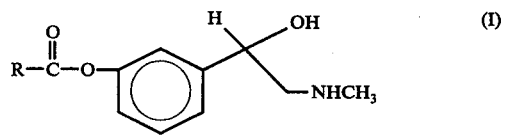

wherein R represents a member selected from the group consisting of an ethoxycarbonyl group and a benzyloxycarbonyl group, or the HX salts thereof, wherein X represents a pharmaceutically acceptable acid addition salt anion in combination with a non-toxic organic or inorganic pharmaceutically acceptable carrier.

3. The composition of claim 2, wherein said carrier is an ophthalmic carrier.

4. The composition of claim 2, wherein said carrier is an inhalation carrier.

5. The composition of claim 2, wherein said carrier is an intranasal carrier.

6. The composition of claim 2, wherein said compound is present in an amount of from 0.01% to 10.0%.

7. The composition of claim 2, wherein said compound is present in an amount of from 5 mgm to 250 mgm, and said carrier is an oral solid or liquid carrier.

8. A method for inducing a sympathomimetic response in a warm-blooded animal in need thereof which comprises administering thereto, a sympathomimetically effective amount of an optically pure and biologically active levorotatory compound of the formula:

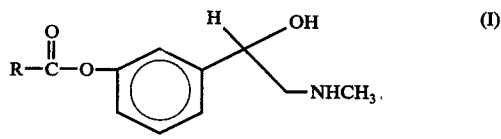

wherein R represents a member selected from the group consisting of an ethoxycarbonyl group and a benzyloxycarbonyl group, of from 1 to 20 carbon atoms or the HX salts thereof, wherein X represents a pharmaceutically acceptable acid addition salt anion.

9. The method of claim 8, wherein said compound is contained in combination with a non-toxic organic or inorganic pharmaceutically acceptable carrier.

10. The method of claim 8, wherein said sympathomimetically effective amount is between 0.01% and 10.0%.

11. The method of claim 9, wherein said non-toxic organic or inorganic pharmaceutically acceptable carrier is an oral carrier.

12. The method of claim 9, wherein said non-toxic organic or inorganic pharmaceutically acceptable carrier is an ophthalmic carrier.

13. The method of claim 8, wherein said sympathomimetic response is mydriasis.

14. The method of claim 8, wherein said sympathomimetic response is a lowering of intraocular pressure.

15. The method of claim 11, wherein said compound is present in an amount of from 5 mgm to 250 mgm.

* * * * *